(12) United States Patent
Katoh

(10) Patent No.: US 6,703,084 B2
(45) Date of Patent: Mar. 9, 2004

(54) QUINONE COMPOUND, LIQUID CRYSTAL COMPOSITION, AND GUEST-HOST-TYPE LIQUID CRYSTAL CELL EMPLOYING THE SAME

(75) Inventor: Takashi Katoh, Kanagawa (JP)

(73) Assignee: Fuji Photo Film Co., Ltd., Minami-Ashigara (JP)

( * ) Notice: Subject to any disclaimer, the term of this patent is extended or adjusted under 35 U.S.C. 154(b) by 62 days.

(21) Appl. No.: 10/125,609

(22) Filed: Apr. 19, 2002

(65) Prior Publication Data

US 2003/0085379 A1 May 8, 2003

(30) Foreign Application Priority Data

Apr. 19, 2001 (JP) .......................... 2001-120566

(51) Int. Cl.$^7$ ...................... C09K 19/60; C07D 307/93; C07D 333/78; C09B 57/00

(52) U.S. Cl. .................. 428/1.3; 252/299.1; 252/299.5; 549/41; 549/456

(58) Field of Search ........................ 428/1.3; 252/299.1, 252/299.5; 549/41, 456; 349/165

(56) References Cited

FOREIGN PATENT DOCUMENTS

JP          2002-338533        * 11/2001

OTHER PUBLICATIONS

CAPLUS 1998: 491766.*
Katsuhira Yoshida et al, "Convenient Synthesis and Dichroic Properties of Heterocyclic Quinone Dyes, 3–(Dialkylamino)benzo[b]naphtho[2,3–d]furan–6, 11–diones", *Chemistry Letters*, pp. 2049–2052 (1990).

Lindsay H. Briggs et al, "Chemistry of Fungi. XI Corticins A, B, and C, Benzobisbenzofurans", *Aust. J. Chem.*, vol. 29, pp. 179–190 (1976).

* cited by examiner

*Primary Examiner*—Shean C. Wu
(74) *Attorney, Agent, or Firm*—Burns, Doane, Swecker & Mathis, LLP

(57) ABSTRACT

A quinone compound represented by formula (1) or (2) below:

Formula (1)

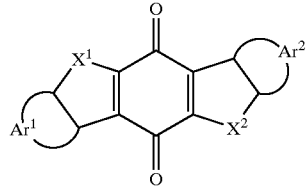

formula (2)

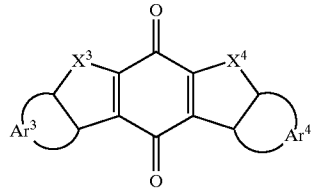

(wherein $X^1$ to $X^4$ independently represents an oxygen atom, sulfur atom or N—$R^1$; $R^1$ represents a hydrogen atom, alkyl group, aryl group or heterocyclic group; $Ar^1$ to $Ar^4$ independently represents an atomic group necessary for forming an aromatic ring or aromatic rings, where at least one of such aromatic rings formed by $Ar^1$ and $Ar^2$ and at least one of such aromatic rings formed by $Ar^3$ and $Ar^4$ have substituent selected from the group consisting of alkylthio group, arylthio group, heteroarylthio group and —N($R^2$)($R^3$) group; and $R^2$ and $R^3$ independently represents a hydrogen atom, alkyl group, aryl group or heterocyclic group, where $R^2$ and $R^3$ may be linked together to form a ring) was disclosed.

40 Claims, No Drawings

QUINONE COMPOUND, LIQUID CRYSTAL COMPOSITION, AND GUEST-HOST-TYPE LIQUID CRYSTAL CELL EMPLOYING THE SAME

TECHNICAL FIELD

The present invention relates to a quinone compound, a liquid crystal composition and a guest-host-type liquid crystal cell employing the same.

RELATED ART

There are known various types of liquid crystal devices (see, for example, "Ekisho Debaisu Handobukku (Liquid Crystal Device Handbook), edited by No. 142 Committee of Japan Society for the Promotion of Science, published by the Nikkan Kogyo Shimbun, Ltd., 1989). For example, guest-host-type liquid crystal device has a cell having filled therein a liquid crystal composition which comprises liquid crystal as host and dichroic dye dissolved therein as guest. When a voltage is applied to the cell sufficient to rotate the liquid crystal molecules, the dye molecules rotate along with the liquid crystal molecules and allow changing of light absorption by the cell to thereby effect display. The reflective liquid crystal device employing guest-host mode is excellent in brightness. The guest-host mode device is disclosed for example in "Handbook of Liquid Crystals", written by B. Bahadur, co to edited by D. Demus, J. Goodby, G. W. Gray, H. W. Spiess, and V. Vill, Vol. 2A, published by Wiley-VCH, 1998, Chapters 3 and 4, p. 257 to 302. Dichromatic dyes available for liquid crystal display are also disclosed in "Dichroic Dyes for Liquid Crystal Display", written by A. V. Ivashchenko, published by CRC, 1994.

Various studies have been made of dichroic dyes of anthraquinone derivatives. In general, anthraquinone dyes however need be dissolved into liquid crystals in a large amount due to their relatively small absorption coefficients, which has often raised a practical problem. So that several studies have been made on other quinone dyes, available as dichroic dye, having molecular skeletons different from those of anthraquinone dye, where reported examples include benzoquinone derivatives and naphthoquinone derivatives. A device using a compound as shown bellow, having a benzofuran ring condensed on one side of a benzoquinone skeleton, as a dichroic dye was disclosed in Yoshida, et al., Chem. Lett., 2049–2052, 1990.

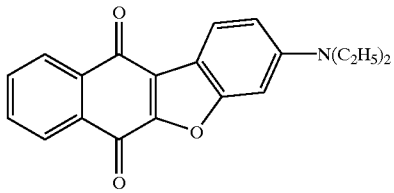

The absorption coefficient of such compound is however still small, so that there is a further demand for improvement. A compound having benzofuran rings condensed on both sides of a benzoquinone skeleton was disclosed in Aust. J. Chem., Vol. 29, p. 179, 1976. Such compound, however, has a methoxy group on the benzofuran ring and thus shows an absorption maximum wavelength at around 300 nm, which cannot allow such compound to be used as a dichroic dye.

It is therefore an object of the present invention to provide a novel quinone compound having a large absorption coefficient. It is another object of the present invention to provide a liquid crystal composition exhibiting a high order parameter. It is still another object of the present invention to provide a guest-host-type liquid crystal cell having an improved contrast of the display.

SUMMARY OF THE INVENTION

The foregoing objects are accomplished by the invention to provide a quinone compound represented by formula (1) or (2) below:

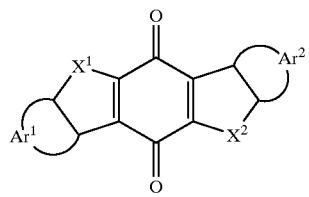

formula (1)

(wherein $X^1$ and $X^2$ independently represents an oxygen atom, sulfur atom or N—$R^1$; $R^1$ represents a hydrogen atom, alkyl group, aryl group or heterocyclic group; $Ar^1$ and $Ar^2$ independently represents an atomic group necessary for forming an aromatic ring or aromatic rings, where at least one of such aromatic rings formed by $Ar^1$ and $Ar^2$ has a substituent selected from the group consisting of alkylthio group, arylthio group, heteroarylthio group and —N($R^2$)($R^3$) group; and $R^2$ and $R^3$ independently represents a hydrogen atom, alkyl group, aryl group or heterocyclic group, where $R^2$ and $R^3$ may be linked together to form a ring); and

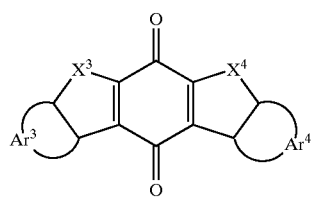

formula (2)

(wherein $X^3$ and $X^4$ independently represents an oxygen atom, sulfur atom or N—$R^4$; $R^4$ represents a hydrogen atom, alkyl group, aryl group or heterocyclic group; $Ar^3$ and $Ar^4$ independently represents an atomic group necessary for forming an aromatic ring or aromatic rings, where at least one of such aromatic rings formed by $Ar^3$ and $Ar^4$ has a substituent selected from the group consisting of alkylthio group, arylthio group, heteroarylthio group and —N($R^5$)($R^6$) group; and $R^5$ and $R^6$ independently represents a hydrogen atom, alkyl group, aryl group or heterocyclic group, where $R^5$ and $R^6$ may be linked together to form a ring).

In the formula (1), $X^1$ and $X^2$, preferably, independently represents an oxygen atom or sulfur atom; both of $X^1$ and $X^2$ are more preferably oxygen atoms.

In the formula (1), $Ar^1$ and $Ar^2$, preferably, respectively represents an atomic group necessary for forming a substituted benzene, naphthalene or pyridine; both of $Ar^1$ and $Ar^2$ are more preferably benzenes substituted by —N($R^2$)($R^3$) group.

In the formula (2), $X^3$ and $X^4$, preferably, independently represents an oxygen atom or sulfur atom; both of $X^3$ and $X^4$ are more preferably oxygen atoms.

In the formula (2), $Ar^3$ and $Ar^4$, preferably, respectively represents an atomic group necessary for forming a substituted benzene, naphthalene or pyridine; both of $Ar^3$ and $Ar^4$ are more preferably benzenes substituted by —$N(R^5)(R^6)$ group.

The present invention further provides a liquid crystal composition comprising at least one liquid crystal compound and at least one quinone compound represented by formula (3) or (4).

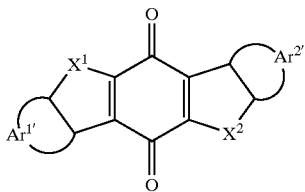

formula (3)

(wherein $X^1$ and $X^2$ independently represents an oxygen atom, sulfur atom or N—$R^1$; $R^1$ represents a hydrogen atom, alkyl group, aryl group or heterocyclic group; $Ar^{1'}$ and $Ar^{2'}$ independently represents an atomic group necessary for forming an aromatic ring or aromatic rings which may be optionally substituted with one or more substituent); and

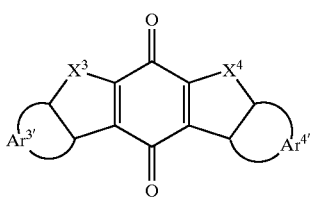

formula (4)

(wherein $X^3$ and $X^4$ independently represents an oxygen atom, sulfur atom or N—$R^4$; $R^4$ represents a hydrogen atom, alkyl group, aryl group or heterocyclic group; $Ar^{3'}$ and $Ar^{4'}$ independently represents an atomic group necessary for forming an aromatic ring or aromatic rings which may be optionally substituted with one or more substituent).

In the formula (3), $X^1$ and $X^2$, preferably, independently represents an oxygen atom or sulfur atom; both of $X^1$ and $X^2$ are more preferably oxygen atoms.

In the formula (3), $Ar^{1'}$ and $Ar^{2'}$, preferably, respectively represents an atomic group necessary for forming a substituted benzene, naphthalene or pyridine; both of $Ar^{1'}$ and $Ar^{2'}$ are more preferably benzenes substituted by —$N(R^2)(R^3)$ group.

In the formula (4), $X^3$ and $X^4$, preferably, independently represents an oxygen atom or sulfur atom; both of $X^3$ and $X^4$ are more preferably oxygen atoms.

In the formula (4), $Ar^{3'}$ and $Ar^{4'}$, preferably, respectively represents an atomic group necessary for forming a substituted benzene, naphthalene or pyridine; both of $Ar^{3'}$ and $Ar^{4'}$ are more preferably benzenes substituted by —$N(R^5)(R^6)$ group.

This invention further provides a guest-host mode liquid crystal cell comprising a liquid crystal layer containing said liquid crystal composition comprising at least one quinone compound represented by said formula (3) or (4).

DETAILED DESCRIPTION OF THE INVENTION

Description will now be given first for the quinone compounds expressed by formulae (1) to (4) bellow, which may occasionally be referred to as "compounds of the present invention".

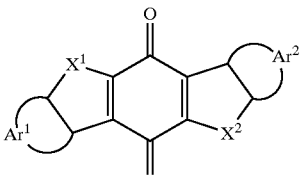

formula (1)

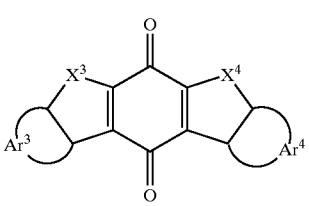

formula (2)

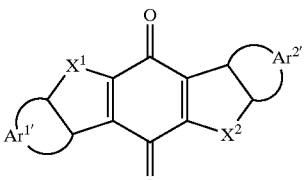

formula (3)

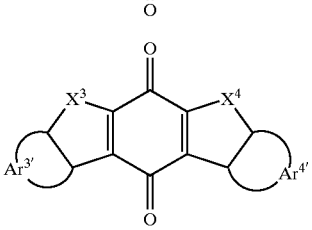

formula (4)

In the formulae (1) and (3), $X^1$ and $X^2$ independently represents an oxygen atom, sulfur atom or N—$R^1$. $R^1$ represents a hydrogen atom, alkyl group, aryl group or heterocyclic group. In the formulae (2) and (4), $X^3$ and $X^4$ independently represents an oxygen atom, sulfur atom or N—$R^4$. $R^4$ represents a hydrogen atom, alkyl group, aryl group or heterocyclic group.

The alkyl groups respectively represented by $R^1$ and $R^4$ include both of substituted alkyl groups and non-substituted alkyl groups, where those having cyclic structure are also included. The alkyl groups are preferably groups having 1 to 40 carbons, more preferably 1 to 12 carbons, and still more preferably 1 to 8 carbons. Specific examples of the alkyl groups include methyl, ethyl, n-propyl, n-butyl, n-pentyl, n-hexyl, n-heptyl, n-octyl, cyclohexyl, 4-methylcyclohexyl, 4-ethylcyclohexyl, 4-propylcyclohexyl, and 4-butylcyclohexyl. The aryl groups respectively represented by $R^1$ and $R^4$ include both of substituted aryl groups and non-substituted aryl groups. The aryl groups are preferably groups having 6–20 carbons, more preferably 6–15 carbons, and still more preferably 6–10 carbons. Specific examples of such aryl groups include phenyl, naphthyl, p-carboxyphenyl, p-nitrophenyl, 3,5-dichlorophenyl, p-cyanophenyl, m-fluorophenyl, and p-tolyl. The heterocyclic groups respectively represented by $R^1$ and $R^4$ include both of substituted heterocyclic groups and non-substituted heterocyclic groups. The heterocyclic groups are preferably groups having 1–20 carbons, more preferably 2 to 10 carbons, and still more preferably 3 to 8 carbons. Specific examples of such heterocyclic groups include pyridyl, 5-methylpyridyl, thienyl, furyl, morphorino, and tetrahydrofurfuryl.

Benzene rings and naphthalene rings thereof may have a condensed structure.

The alkyl groups, aryl groups or heterocyclic groups may have one or more substituent. Generalizing now the substituent as substituent group "Y", such substituent group "Y" includes halogen atoms (e.g., chlorine, bromine, iodine, fluorine); mercapto group; cyano group; carboxyl group; phosphoric acid group; sulfonic acid group; hydroxyl group; carbamoyl groups having $C_{1-10}$, preferably $C_{2-8}$, more preferably $C_{2-5}$ (e.g., methylcarbamoyl, ethylcarbamoyl, morpholinocarbamoyl); sulfamoyl groups having $C_{0-10}$, preferably $C_{2-8}$, and more preferably $C_{2-5}$ (e.g., methylsulfamoyl, ethylsulfamoyl, piperidinosulfamoyl); nitro group; alkyl groups having $C_{1-40}$, preferably $C_{1-12}$, more preferably $C_{1-8}$ (e.g., methyl, ethyl, propyl, butyl, pentyl, hexyl, heptyl, octyl, cyclohexyl, 4-methylcyclohexyl, 4-ethylcyclohexyl, 4-propylcyclohexyl, 4-butylcyclohexyl); alkoxy groups having $C_{1-20}$, preferably $C_{1-10}$, more preferably $C_{1-8}$ (e.g., methoxy, ethoxy, 2-methoxyethoxy, 2-phenylethoxy); aryloxy groups having $C_{6-20}$, preferably $C_{6-12}$, more preferably $C_{6-10}$ (e.g., phenoxy, p-methylphenoxy, p-chlorophenoxy, naphthoxy); acyl groups having $C_{1-20}$, preferably $C_{2-12}$, more preferably $C_{2-8}$ (e.g., acetyl, benzoyl, trichloroacetyl); acyloxy groups having $C_{1-20}$, preferably $C_{2-12}$, more preferably $C_{2-8}$ (e.g., acetyloxy, benzoyloxy); acylamino groups having $C_{1-20}$, preferably $C_{2-12}$, more preferably $C_{2-8}$ (e.g., acetylamino); sulfonyl groups having $C_{1-20}$, preferably $C_{1-10}$, more preferably $C_{1-8}$ (e.g., methanesulfonyl, ethanesulfonyl, benzenesulfonyl); sulfinyl groups having $C_{1-20}$, preferably $C_{1-10}$, more preferably $C_{1-8}$ (e.g., methanesulfinyl, ethanesulfinyl, benzenesulfinyl); sulfonylamino groups having $C_{1-20}$, preferably $C_{1-10}$, more preferably $C_{1-8}$ (e.g., methanesulfonylamino, ethanesulfonylamino, benzenesulfonylamino); amino groups having $C_{0-20}$, preferably $C_{1-12}$, more preferably $C_{1-8}$ (e.g., amino, methylamino, dimethylamino, benzylamino, anilino, diphenylamino); ammonium groups having $C_{0-15}$, preferably $C_{3-10}$, more preferably $C_{3-6}$ (e.g., trimethylammonium, triethylammonium); hydrazino groups having $C_{0-15}$, preferably $C_{1-10}$, more preferably $C_{1-6}$ (e.g., trimethylhydrazino); ureido groups having $C_{1-15}$, preferably $C_{1-10}$, more preferably $C_{1-6}$ (e.g., ureido, N,N-dimethylureido); imido groups having $C_{1-15}$, preferably $C_{1-10}$, more preferably $C_{1-6}$ (e.g., succinimide); alkylthio groups having $C_{1-20}$, preferably $C_{1-12}$, more preferably $C_{1-8}$ (e.g., methylthio, ethylthio, propylthio); carbonarylthio and heteroarylthio groups having $C_{1-20}$, preferably $C_{2-12}$, more preferably $C_{5-10}$ (e.g., phenylthio, p-methylphenylthio, p-chlorophenylthio, 2-pyridylthio, naphtylthio); alkoxycarbonyl groups having $C_{2-20}$, preferably $C_{2-12}$, more preferably $C_{2-8}$ (e.g., methoxycarbonyl, ethoxycarbonyl, 2-benzyloxylcarbonyl); aryloxycarbonyl groups having $C_{6-20}$, preferably $C_{6-12}$, more preferably $C_{6-10}$ (e.g., phenoxycarbonyl); aryl groups having $C_{6-20}$, preferably $C_{6-15}$, more preferably $C_{6-10}$ (e.g., phenyl, naphthyl, p-carboxyphenyl, p-nitrophenyl, 3,5-dichlorophenyl, p-cyanophenyl, m-fluorophenyl, p-tolyl); and substituted or non-substituted heterocyclic groups having $C_{1-20}$, preferably $C_{2-10}$, more preferably $C_{4-6}$ (e.g., pyridyl, 5-methylpyridyl, thienyl, furyl, morpholino, tetrahydrofurfuryl, quinolyl, thiazolyl, benzothiazolyl, oxazolyl, benzooxyazolyl, imidazolyl, benzoimidazolyl). Structures having condensed benzene rings or naphthalene rings are also allowable.

The alkyl group, aryl group and heterocyclic group respectively represented by $R^1$ and $R^4$ are preferably not substituted or substituted with halogen atoms, alkyl groups, aryl groups or alkoxy groups; and more preferably not substituted or substituted with a fluorine atom, chlorine atom, butyl, cyclohexyl, trifluoromethyl, phenyl or trifluoromethoxy.

In the forgoing formulae (1) to (4), $X^1$, $X^2$, $X^3$ and $X^4$ preferably respectively represents an oxygen atom or sulfur atom, and more preferably represent oxygen atoms.

In the foregoing formulae (1) to (4), $Ar^1$, $Ar^2$, $Ar^3$, $Ar^4$, $Ar^{1'}$, $Ar^{2'}$, $Ar^{3'}$ and $Ar^{4'}$ independently represents atomic group necessary for forming aromatic rings.

The atomic group respectively represented by $Ar^1$ to $Ar^4$ and $Ar^{1'}$ to $Ar^{4'}$ may be composed of carbon atoms only, or may be composed of carbon atoms and hetero-atoms selected from oxygen atom, nitrogen atom, sulfur atom and so forth. That is, the aromatic rings formed by $Ar^1$ to $Ar^4$ and $Ar^{1'}$ to $Ar^{4'}$ include both of carbonaromatic rings and heteroaromatic rings. The aromatic rings include both of monocyclic and condensed rings. Examples of the carbonaromatic rings include benzene, naphthalene and anthracene. Examples of the heteroaromatic rings include pyridine, quinoline, isoquinoline, pyrimidine, pyrazine, oxazole, thiazole, imidazole, pyrazole, oxadiazole, thiadiazole, triazole, and condensed rings formed by condensation of two or more heteroaromatic rings, or condensation of at least one heteroaromatic ring and the foregoing carbonaromatic rings. Of these, benzene, naphthalene and pyridine are more preferable, and benzene is still more preferable.

The aromatic rings formed by $Ar^1$ to $Ar^4$ and $Ar^{1'}$ to $Ar^{4'}$ may have one or more substituent, and such substituent may be selected from the foregoing substituent group "Y".

In the formula (1), at least one of such aromatic rings formed by $Ar^1$ and $Ar^2$ has an alkylthio group, arylthio group, heteroarylthio group or $-N(R^2)(R^3)$ group as a substituent, and in the formula (2), at least one of such aromatic rings formed by $Ar^3$ and $Ar^4$ has an alkylthio group, arylthio group, heteroarylthio group or $-N(R^5)(R^6)$ group as a substituent. $R^2$, $R^3$, $R^5$ and $R^6$ independently represents a hydrogen atom, alkyl group, aryl group or heterocyclic group, where $R^2$ and $R^3$, or $R^5$ and $R^6$ may be linked together to form a ring. The alkyl groups composing the alkylthio groups may be those respectively represented by $R^1$ and $R^4$, and the preferable examples thereof may be the same. Specific examples of the alkylthio groups include methylthio, ethylthio, propylthio and n-butylthio. The aryl groups composing the arylthio groups may be those respectively represented by $R^1$ and $R^4$, and specific examples thereof may be the same. Specific examples of the arylthio groups include phenylthio, p-chlorophenylthio, p-bromophenylthio and p-methylphenylthio. The heteroaryl groups composing the heteroarylthio groups can be exemplified by heteroaromatic rings respectively formed by $Ar^1$ to $Ar^4$. Specific examples of the heteroarylthio group include 2-pyridylthio group.

The alkyl group, aryl group and heterocyclic group respectively represented by $R^2$, $R^3$, $R^5$ and $R^6$ may be those represented by $R^1$ and $R^4$, and specific examples maybe the same. The foregoing alkyl group, aryl group and heterocyclic group may respectively have one ore more substituent, where the substituent can be exemplified by the foregoing substituent group "Y". $R^2$ and $R^3$, or $R^5$ and $R^6$ may be linked together to thereby form a ring. Specific examples of $-N(R^2)(R^3)$ groups and $-N(R^5)(R^6)$ groups include dimethylamino, diethylamino, morpholino, piperadino, benzylamino, diphenylamino and 2-benzothiazolylamino.

The aromatic rings formed by $Ar^1$ to $Ar^4$ preferably have arylthio groups or dialkylamino groups.

The aromatic rings formed by $Ar^{1'}$, $Ar^{2'}$, $Ar^{3'}$ and $Ar^{4'}$ may have substituent. Preferred substituent for $Ar^{1'}$ to $Ar^{4'}$ are the same as described for $Ar^1$ to $Ar^4$.

Specific examples of the quinone compounds expressed by the foregoing formulae (1) to (4) will be listed below, which by no means restricts the present invention.

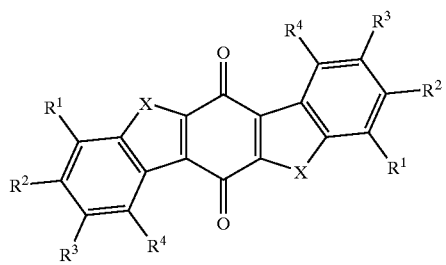
| No. | R$^1$ | R$^2$ | R$^3$ | R$^4$ | X |
|---|---|---|---|---|---|
| 1-1 | H | H | NEt$_2$ | H | O |
| 1-2 | Cl | H | NHEt | H | O |
| 1-3 | H | F | —N(morpholine) | H | O |
| 1-4 | n-Bu | H | —N(4-Ph-piperidine) | H | O |
| 1-5 | H | H | H | NMe$_2$ | O |
| 1-6 | H | H | NMe$_2$ | H | S |
| 1-7 | CF$_3$ | H | NPh$_2$ | H | O |
| 1-8 | H | H | —HN-(3-pyridyl) | H | O |
| 1-9 | H | Me | NMe$_2$ | Me | O |
| 1-10 | cyclohexyl | H | SMe | H | O |
| 1-11 | H | H | —S-Ph | H | O |
| 1-12 | H | H | —S-(4-(n)Bu-C$_6$H$_4$) | H | O |
| 1-13 | H | H | —S-(4-(t)Bu-C$_6$H$_4$) | H | O |
| 1-14 | phenyl | H | H | SMe | O |
| 1-15 | H | H | —S-(3-pyridyl) | H | S |
| 1-16 | Cl | SMe | H | H | O |
| 1-17 | SMe | H | NMe$_2$ | H | O |
| 1-18 | SEt | Me | NMe$_2$ | Me | O |

-continued
1-19
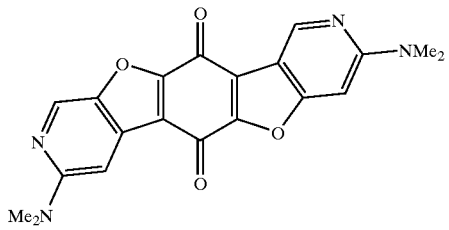
1-20
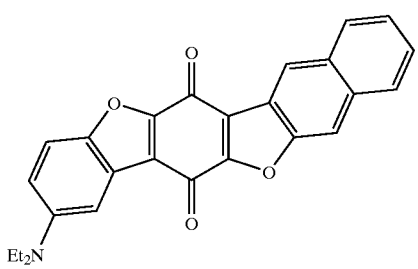
1-21
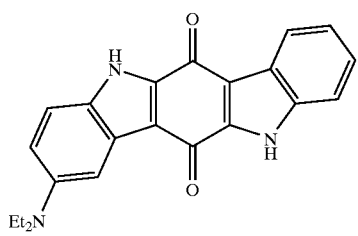
1-22
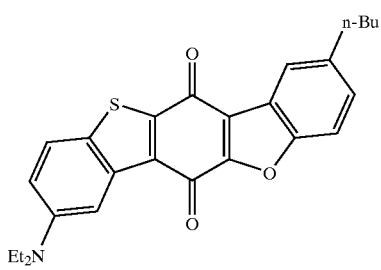
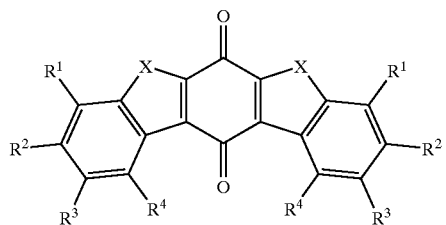
| No. | R$^1$ | R$^2$ | R$^3$ | R$^4$ | X |
|---|---|---|---|---|---|
| 2-1 | H | H | NEt$_2$ | H | O |
| 2-2 | Cl | H | NHEt | H | S |
| 2-3 | OCF$_3$ | H | —N(morpholino) | H | O |
| 2-4 | H | H | —N(4-Ph-piperidino) | H | NH |
| 2-5 | H | H | H | NMe$_2$ | O |
| 2-6 | H | n-C$_4$F$_9$ | NMe$_2$ | H | S |

| | | | | | |
|---|---|---|---|---|---|
| 2-7 | H | H | NPh$_2$ | H | NMe |
| 2-8 | H | H | —HN—(3-pyridyl) | H | O |
| 2-9 | H | H | SMe | H | O |
| 2-10 | Cl | H | SEt | H | S |
| 2-11 | H | H | —S—Ph | H | O |
| 2-12 | n-Bu | H | —S—C$_6$H$_4$—(n)Bu | H | NH |
| 2-13 | H | H | H | SEt | O |
| 2-14 | H | SMe | NMe$_2$ | H | S |
| 2-15 | H | Ph | SBu-n | H | NMe |
| 2-16 | H | H | SBu-n | H | O |

2-17

2-18

2-19

The compounds of the present invention can be synthesized by condensation reaction of benzoquinone derivatives with a substituted phenol, substituted thiophenol or substituted aniline compounds. Using the substituted phenol yields a compound comprising a benzoquinone derivative condensed with benzofuran ring, using the substituted thiophenol yields that condensed with a benzothiophene ring, and using the substituted aniline yields that condensed with a benzopyrrole ring. The available benzoquinone derivatives include benzoquinone or benzoquinone having an eliminative group, where tetrachlorobenzoquinone is one preferable example of such benzoquinone derivatives having an eliminative group. The foregoing condensation reaction can be subjected to in any of basic, neutral and acidic reaction systems, where basic system is more preferable. The available bases include inorganic base (e.g., sodium hydroxide, potassium hydroxide, NaOMe), and organic bases (e.g., triethylamine, pyridine). Combination of the inorganic and organic bases is also allowable.

Reaction solvent for the condensation reaction may be any of water, organic solvent, and double-phase water/organic system, where organic solvent is more preferable.

Although not being specifically limited, available organic solvents include alcoholic solvents such as methanol and ethanol; ether solvents such as diethylether, tetrahydrofuran and dioxane; aromatic solvents such as benzene, toluene and xylene; hydrocarbon solvents such as hexane and pentane; halogenated hydrocarbon solvents such as chloroform and methylene chloride; nitrile solvents such as acetonitrile and benzonitrile; amide solvents such as dimethylformamide and dimethylacetamide; ester solvents such as ethyl acetate; and sulfoxide solvents such as dimethylsulfoxide; where mixing of two or more solvents is also allowable. Preferable reaction solvents include alcoholic solvent, nitrile solvents, ether solvents and halogenated hydrocarbon solvents, and specific examples thereof include methanol, ethanol, acetonitrile, tetrahydrofuran, chloroform and methylene chloride, and more preferably methanol and ethanol.

While concentration of the reaction solution is not specifically limited, it is generally preferable that the benzoquinone derivative as a source material is contained in the solvent in a concentration of 0.1 mmol/L to 10 mol/L, and more preferably 1 mmol/L to 0.1 mol/L. Reaction temperature is preferably −20 to 100° C., more preferably −5 to 50° C., and still more preferably 0 to 20° C., although being not specifically limited.

The liquid crystal composition of the present invention is characterized in that containing the compound of the present invention. The compound of the present invention has a large absorption coefficient, which can thus improve order parameter of the liquid crystal composition. In particular, using such compound as a dichroic dye for a guest-host mode liquid crystal display will successfully improve contrast.

For the liquid crystal composition of the present invention, the compound represented by the formula (3) or (4) may be used individually, or in any combinations of two or more species. For the case of using two or more species, two or more compounds of the present invention may be mixed, or the compound of the present invention may be mixed with other known dichroic dye. Description of such known dichroic dyes available for the mixed use are typically found in "Dichroic Dyes for Liquid Crystal Display", written by A. V. Ivashchenko, published by CRC, 1994. In order to apply the liquid crystal composition of the present invention to a black-and-white display, it is preferable to use two or more dichroic dyes as mixed so that they can cooperatively absorb the light over the entire visible wavelength range.

While there is no specific limitation on the host liquid crystal (liquid crystal compound) available for the composition of the present invention, typical examples thereof include those exhibiting nematic phase or smectic phase. Specific examples thereof include azomethine compounds, cyanobiphenyl compounds, cyanophenyl esters, fluorine-substituted phenyl esters, cyclohexanecarboxylic acid phenyl esters, fluorine-substituted cyclohexanecarboxylic acid phenyl esters, cyanophenylcyclohexanes, fluorine-substituted phenylcyclohexanes, cyano-substituted phenylpyrimidines, fluorine-substituted phenylpyrimidines, alkoxy-substituted phenylpyrimidines, fluorine-substituted-alkoxy-substituted phenylpyrimidines, phenyldioxanes, tolan compounds, fluorine-substituted tolan compounds and alkenylcyclohexyl benzonitriles. Available examples of the liquid crystal compounds are found in "Ekisho Debaisu Handobukku (Liquid Crystal Device Handbook), edited by No. 142 Committee of Japan Society for the Promotion of Science, published by the Nikkan Kogyo Shimbun, Ltd., 1989, p. 154–192, and p. 715–722. It is also allowable to use the fluorine-substituted host liquid crystal such as MLC-6267, 6284, 6287, 6288, 6406, 6422, 6423, 6425, 6435, 6437, 7700, 7800, 9000, 9100, 9200, 9300, 10000, 12200, ZLI-4692 (the above are supplied by Merck), LIXON 5036XX, 5037XX, 5039XX, 5040XX, 5041XX, (the above are supplied by Chisso) etc., which is suitable for TFT driving.

The liquid crystal composition of the present invention may be added with a compound showing no liquid crystalline property in order to adjust physical properties of the host liquid crystal (typically in order to adjust the temperature range, in which the liquid crystal phase appears, to a desirable range). It is also allowable to add other compounds such as chiral compound, UV absorber and antioxidant. Typical examples thereof relate to chiral agents for twisted-nematic (TN) and super-twisted-nematic (STN) liquid crystals, which can typically be found in "Ekisho Debaisu Handobukku (Liquid Crystal Device Handbook), edited by No. 142 Committee of Japan Society for the Promotion of Science, published by the Nikkan Kogyo Shimbun, Ltd., 1989, p. 199–202.

While there is no specific limitation on the content of the host liquid crystal and the compound of the present invention, the content of the compound of the present invention is preferably 0.1 to 15 wt % with respect to the content of the host liquid crystal, and more preferably 0.5 to 6 wt %.

The liquid crystal composition of the present invention can be prepared by dissolving the compound of the present invention into the host liquid crystal. The dissolution can be attained with the aid of mechanical stirring, heating, ultrasonic vibration and any combinations thereof.

The guest-host-type liquid crystal cell of the present invention has a liquid crystal layer containing the liquid crystal composition of the present invention.

One embodiment of the present invention is a liquid crystal cell comprising a pair of electrode substrates and a liquid crystal layer sandwiched between such electrode substrates, which contains the liquid crystal composition of the present invention. The electrode substrate generally comprises a glass substrate or plastic substrate, and an electrode layer formed thereon. Materials available for composing the plastic substrate include acryl resin, polycarbonate resin, epoxy resin and so forth. Available examples of such substrate are typically found in "Ekisho Debaisu Handobukku (Liquid Crystal Device Handbook), edited by No. 142 Committee of Japan Society for the Promotion of Science, published by the Nikkan Kogyo Shimbun, Ltd., 1989, p. 218–231. The electrode layer formed on the substrate is preferably a transparent electrode layer. Materials available for composing such electrode layer include indium oxide, indium tin oxide (ITO), tin oxide and so forth. Available examples of the transparent electrode are typically found in "Ekisho Debaisu Handobukku (Liquid Crystal Device Handbook), edited by No. 142 Committee of Japan Society for the Promotion of Science, published by the Nikkan Kogyo Shimbun, Ltd., 1989, p. 232–239.

The surface of the substrate to be brought into contact with the liquid crystal layer preferably has formed thereon a layer subjected to treatment for controlling orientation of the liquid crystal molecules (alignment film). The treatment can be effected by coating of a quaternary ammonium salt solution, rubbing a coated polyimide film, by oblique vapor deposition of $SiO_x$, and photo irradiation based on photo-isomerization reaction. Available examples of the alignment film can typically be found in "Ekisho Debaisu Handobukku (Liquid Crystal Device Handbook), edited by No. 142 Committee of Japan Society for the Promotion of Science, published by the Nikkan Kogyo Shimbun, Ltd., 1989), p. 240–256.

The liquid crystal cell of the present invention can be fabricated by opposing a pair of substrates at a distance of 1 to 50 μm as being typically interposed with a spacer, and filling the liquid crystal composition of the present invention in the space formed between such substrates. Available examples of the spacer can typically be found in "Ekisho Debaisu Handobukku (Liquid Crystal Device Handbook), edited by No. 142 Committee of Japan Society for the Promotion of Science, published by the Nikkan Kogyo Shimbun, Ltd., 1989), p. 257–262.

The liquid crystal cell of the present invention can be driven based on simple matrix driving system or active matrix driving system using thin film transistors (TFT) or the like. Examples of the driving systems applicable to the liquid crystal cell of the present invention can typically be found in "Ekisho Debaisu Handobukku (Liquid Crystal Device Handbook), edited by No. 142 Committee of Japan Society for the Promotion of Science, published by the Nikkan Kogyo Shimbun, Ltd., 1989), p. 387–460.

The liquid crystal cell of the present invention can be applicable to liquid crystal display. While the display modes thereof are not specifically limited, representative systems described in "Ekisho Debaisu Handobukku (Liquid Crystal Device Handbook), edited by No. 142 Committee of Japan Society for the Promotion of Science, published by the Nikkan Kogyo Shimbun, Ltd., 1989, p. 309 include those based on (1) homogeneous orientation and (2) homeotropic orientation, both of which being classified in the guest-host-type; and (3) focalconic orientation and (4) homeotropic orientation, both of which being classified in White-Taylor-type (phase transition); (5) combination with STN crystal; and (6) combination with ferroelectric liquid crystal (FLC). Guest-host (GH) mode display is also available, and "Hansha-gata Kara LCD Sogo Gijutsu (General Technologies of Reflection-type Color LCD)", supervised by Tatsuo Uchida, published by CMC, 1999, Chapter 2-1 "GH-mode, Reflective mode Color LCD", p. 15–16 describes specific examples thereof, which include those of (1) Heilmeier mode,, (2) quarter-wave plate mode, (3) double layer mode, (4) phase transition mode, and (5) polymer-dispersed liquid crystal (PDLC) mode.

The liquid crystal cell of the present invention may be applied in a liquid crystal display of multiple layered GH mode such as disclosed in JP-A-10-67990, JP-A-10-239702, JP-A-10-133223, JP-A-10-339881, JP-A-11-52411, JP-A-11-64880 and JP-A-2000-221538 (the term "JP-A" as used herein means an "unexamined published Japanese patent application"), and in a liquid crystal display of GH mode using microcapsules such as disclosed in JP-A-11-24090. Furthermore, the liquid crystal cell may be applied in a reflective mode liquid crystal display such as disclosed in JP-A-6-235931, JP-A-6-235940, JP-A-6-265859, JP-A-7-56174, JP-A-9-146124, JP-A-9-197388, JP-A-10-20346, JP-A-10-31207, JP-A-10-31216, JP-A-10-31231, JP-A-10-31232, JP-A-10-31233, JP-A-10-31234, JP-A-10-82986, JP-A-10-90674, JP-A-10-111513, JP-A-10-111523, JP-A-10-123509, JP-A-10-123510, JP-A-10-206851, JP-A-10-253993, JP-A-10-268300, JP-A-11-149252 and JP-A-2000-2874; and in a liquid polymer-dispersed liquid crystal (PDLC) mode such as disclosed in JP-A-5-61025, JP-A-5-265053, JP-A-6-3691, JP-A-6-23061, JP-A-5-203940, JP-A-6-242423, JP-A-6-289376, JP-A-8-278490 and JP-A-9-813174.

The liquid crystal composition of the present invention is also applicable to spatial light modulator, and liquid crystal display of optically-addressed or thermally-addressed type.

EXAMPLES

The present invention will be specifically explained with reference to the following examples. The materials, regents, ratios, procedures and so forth shown in the following examples can be optionally changed so long as such change does not depart from the spirit of the present invention. Therefore, the scope of the present invention is not limited by the following examples.

Example 1

Exemplary Synthesis of Compounds 1-1 and 2-1

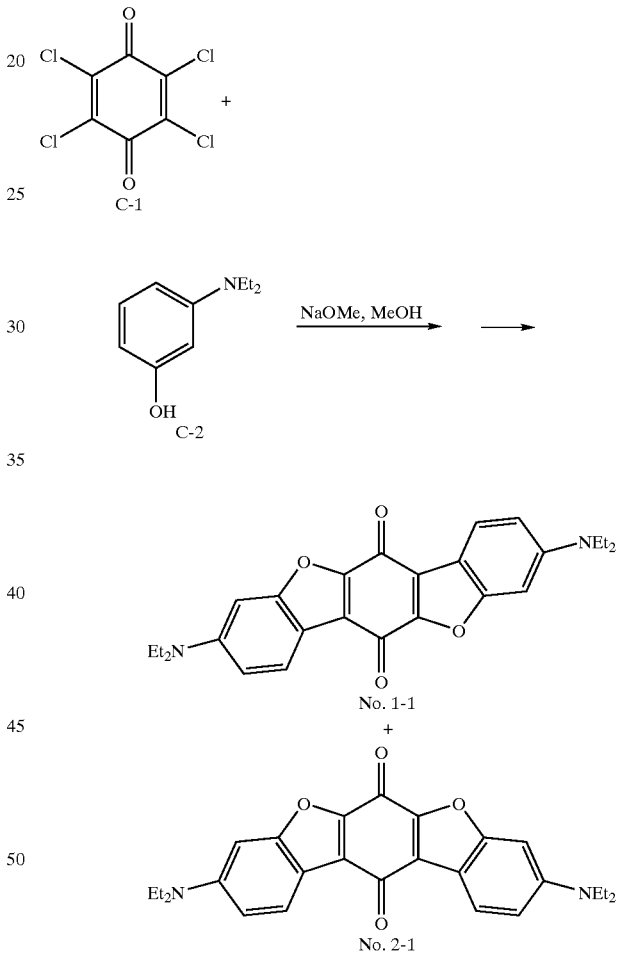

Under a nitrogen environment, 4.2 ml of a 28% NaOMe solution in methanol was dropped into 50 ml of methanol containing 1.20 g of source material (C-1) and 1.80 g of source material (C-2) at room temperature, and the obtained mixture was then refluxed for 6 hours under stirring. The reaction mixture was cooled, added with water, organic components contained therein was then extracted with methylene chloride, the organic phase was dried with magnesium sulfate, and the solvent was evaporated under reduced pressure. The obtained residue was carefully isolated and purified by silica gel chromatography (eluted with chloroform-hexane), to thereby obtain 0.42 g of target compound (1-1) and 0.10 g of target compound (2-1). Properties of the individual compounds are listed below.

Compound (1-1)

purple crystal, m.p. 288° C.

Absorption maximum=550 nm (in acetonitrile)

Absorption coefficient=18,200

H-NMR(CDCl$_3$) d:1.2 (t,12h), 3.4 (q,8h), 6.7 (s,2h), 6.8 (d, 2h) 7.9 (d,2h)

Compound (2-1)

Red crystal, m.p. 292° C.

Absorption maximum=520 nm (in acetonitrile)

Absorption coefficient=18,000

H-NMR(CDCl$_3$) d:1.2 (t,12h), 3.4 (q,8h), 6.5 (s,2h), 6.7 (d, 2h), 8.9 (d,2 h)

A comparative compound M-1, 2,6-diethylamino-anthraquinone, showed an absorption maximum wavelength of 430 nm and an absorption coefficient of 14,200.

The compounds 1-1 and 2-1 were found to have larger absorption coefficients than that of a correspondent anthraquinone dye.

Example 2

Each of the compounds listed in Table 1 below in an amount of 1.0 mg was dissolved in 100 mg of a liquid crystal ZLI-1132 (trade name, a product of E. Merck) to thereby prepare a liquid crystal composition. The obtained liquid crystal composition was then filled in a commercial liquid crystal cell to thereby fabricate a guest-host-type liquid crystal cell or a comparative liquid crystal cell. The liquid crystal cell employed herein was a product of E. H. C. Corporation, which comprises a pair of glass plates (0.7 mm thick) having formed thereon ITO transparent electrode layers and polyimide alignment films (patterned in parallel by rubbing treatment), has a cell gap of 8 μm, and has a epoxy resin seal.

Each of thus fabricated liquid crystal cells 1 and 2 of the present invention and each of the comparative liquid crystal cells 1 and 2 was respectively irradiated with polarized lights in parallel to and perpendicular to the direction of rubbing, and respective absorption spectra (A∥ and A⊥) were measured using a spectrophotometer Model UV3100 (product of Shimadzu Corporation). Based on A∥ and A⊥, the order parameter S was calculated using the equation 1 below. Thus calculated order parameters S were listed in Table 1 together with absorption maximum wavelengths ($\lambda_{max}$).

$$S=(A\|-A\perp)/(A\|+2\times A\perp)$$ quation 1

Compound M-1 (J. Phys. Chem., Vol. 98, p. 4,511, 1994) and compound M-2 (Chem. Lett., p. 2049, 1990) were used for comparison.

TABLE 1

| | Dichronic Dye | Absorption Maximum Wavelength (nm) | Order Parameter S | Remarks |
|---|---|---|---|---|
| LC Device 1 | No. 1-1 | 560 | 0.66 | This invention |
| LC Device 2 | No. 2-1 | 525 | 0.61 | This invention |

TABLE 1-continued

| | Dichronic Dye | Absorption Maximum Wavelength (nm) | Order Parameter S | Remarks |
|---|---|---|---|---|
| LC Device 3 | No. 1-13 | 520 | 0.63 | This invention |
| Comparative LC Device 1 | M-1 | 430 | 0.45 | Comparative Example |
| Comparative LC Device 2 | M-2 | 570 | 0.55 | Comparative Example |

Comparative Dye M-1

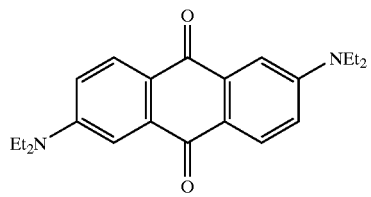

Comparative Dye M-2

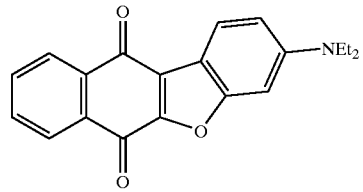

Example 3

The compound 1-1 of the present invention was dissolved in a fluorine-containing liquid crystal ZLI-4972 (trade name, product of E. Merck), and the order parameter S was measured according to a procedure similarly in Example 1, which was found to be S=0.66.

It was thus made clear that the compound 1-1 showed a large order parameter even when being used together with a fluorine-containing host liquid crystal.

It was thus concluded that the present invention was successful in providing a novel quinone compound having a large absorption coefficient, and also in providing a liquid crystal composition having a large order parameter.

Having described our invention as related to the present embodiments, it is our intention that the invention not be limited by any of the details of the description, unless otherwise specified, but rather be construed broadly within its spirit and scope as set out in the accompanying claims.

What is claimed is:

1. A liquid crystal composition comprising at least one liquid crystal compound and at least one quinone compound represented by formula (3) or (4) below:

formula (3)

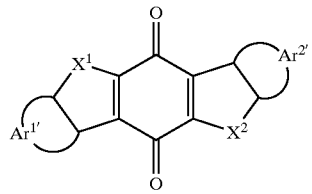

(wherein $X^1$ and $X^2$ independently represents an oxygen atom, sulfur atom or N—$R^1$; $R^1$ represents a hydrogen atom, alkyl group, aryl group or heterocyclic group; $Ar^{1\prime}$ and $Ar^{2\prime}$ independently represents an atomic group necessary for forming an aromatic ring or aromatic rings which may be optionally substituted with one or more substituent); and formula (4)

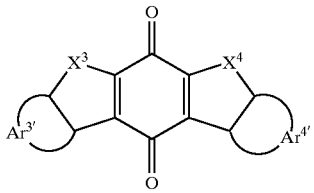

(wherein $X^3$ and $X^4$ independently represents an oxygen atom, sulfur atom or N—$R^4$; $R^4$ represents a hydrogen atom, alkyl group, aryl group or heterocyclic group; $Ar^{3\prime}$ and $Ar^{4\prime}$ independently represents an atomic group necessary for forming an aromatic ring or aromatic rings which may be optionally substituted with one or more substituent).

2. The liquid crystal composition of claim 1, wherein the quinone compound is represented by said formula (3).

3. The liquid crystal composition of claim 1, wherein the quinone compound is represented by said formula (4).

4. The liquid crystal composition of claim 2, wherein $X^1$ and $X^2$ in the formula (3) independently represents an oxygen atom or sulfur atom.

5. The liquid crystal composition of claim 3, wherein $X^3$ and $X^4$ in the formula (4) independently represents an oxygen atom or sulfur atom.

6. The liquid crystal composition of claim 2, wherein both of $X^1$ and $X^2$ in the formula (3) are oxygen atoms.

7. The liquid crystal composition of claim 3, wherein both of $X^3$ and $X^4$ in the formula (4) are oxygen atoms.

8. The liquid crystal composition of claim 2, wherein $Ar^{1\prime}$ and $Ar^{2\prime}$ respectively represents an atomic group necessary for forming a substituted benzene, naphthalene or pyridine.

9. The liquid crystal composition of claim 3, wherein $Ar^{3\prime}$ and $Ar^{4\prime}$ respectively represents an atomic group necessary for forming a substituted benzene, naphthalene or pyridine.

10. The liquid crystal composition of claim 2, wherein both of $Ar^{1\prime}$ and $Ar^{2\prime}$ are substituted by at least one alkylthio group, arylthio group, heteroarylthio group and —N($R^2$)($R^3$) group, wherein $R^2$ and $R^3$ independently represents a hydrogen atom, alkyl group, aryl group or heterocyclic group, where $R^2$ and $R^3$ may be linked together to form a ring.

11. The liquid crystal composition of claim 3, wherein both of $Ar^{3\prime}$ and $Ar^{4\prime}$ are substituted by at least one alkylthio group, arylthio group, heteroarylthio group and —N($R^5$)($R^6$) group, wherein $R^5$ and $R^6$ independently represents a hydrogen atom, alkyl group, aryl group or heterocyclic group, where $R^5$ and $R^6$ may be linked together to form a ring.

12. The liquid crystal composition of claim 1, wherein the content of the quinone compound is from 0.1 to 15 wt % based on the total weight of the liquid crystal compound.

13. The liquid crystal composition of claim 1, wherein said liquid crystal compound is a fluorine-containing liquid crystal compound.

14. A guest-host mode liquid crystal cell comprising a liquid crystal layer containing at least one liquid crystal compound and at least one quinone compound represented by formula (3) or (4) below:

formula (3)

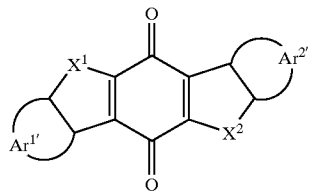

(wherein $X^1$ and $X^2$ independently represents an oxygen atom, sulfur atom or N—$R^1$; $R^1$ represents a hydrogen atom, alkyl group, aryl group or heterocyclic group; $Ar^{1\prime}$ and $Ar^{2\prime}$ independently represents an atomic group necessary for forming an aromatic ring or aromatic rings which may be optionally substituted with one or more substituent); and formula (4)

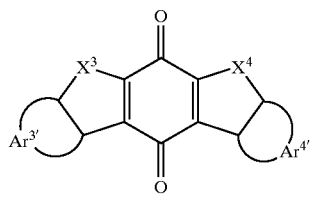

(wherein $X^3$ and $X^4$ independently represents an oxygen atom, sulfur atom or N—$R^4$; $R^4$ represents a hydrogen atom, alkyl group, aryl group or heterocyclic group; $Ar^{3\prime}$ and $Ar^{4\prime}$ independently represents an atomic group necessary for forming an aromatic ring or aromatic rings which may be optionally substituted with one or more substituent).

15. The guest-host mode liquid crystal cell of claim 14, wherein the quinone compound is represented by said formula (3).

16. The guest-host mode liquid crystal cell of claim 14, wherein the quinone compound is represented by said formula (4).

17. The guest-host mode liquid crystal cell of claim 15, wherein $X^1$ and $X^2$ in the formula (3) independently represents an oxygen atom or sulfur atom.

18. The guest-host mode liquid crystal cell of claim 16, wherein $X^3$ and $X^4$ in the formula (4) independently represents an oxygen atom or sulfur atom.

19. The guest-host mode liquid crystal cell of claim 15, wherein both of $X^1$ and $X^2$ in the formula (3) are oxygen atoms.

20. The guest-host mode liquid crystal cell of claim 16, wherein both of $X^3$ and $X^4$ in the formula (4) are oxygen atoms.

21. The guest-host mode liquid crystal cell of claim 15, wherein $Ar^{1\prime}$ and $Ar^{2\prime}$ respectively represents an atomic group necessary for forming a substituted benzene, naphthalene or pyridine.

22. The guest-host mode liquid crystal cell of claim 16, wherein $Ar^{3\prime}$ and $Ar^{4\prime}$ respectively represents an atomic group necessary for forming a substituted benzene, naphthalene or pyridine.

23. The guest-host mode liquid crystal cell of claim 15, wherein both of $Ar^{1\prime}$ and $Ar^{2\prime}$ are substituted by at least one alkylthio group, arylthio group, heteroarylthio group and —N($R^2$)($R^3$) group, wherein $R^2$ and $R^3$ independently represents a hydrogen atom, alkyl group, aryl group or heterocyclic group, where $R^2$ and $R^3$ may be linked together to form a ring.

24. The guest-host mode liquid crystal cell of claim 16, wherein both of $Ar^{3\prime}$ and $Ar^{4\prime}$ are substituted by at least one alkylthio group, arylthio group, heteroarylthio group and —N(R⁵)(R⁶) group, wherein R⁵ and R⁶ independently represents a hydrogen atom, alkyl group, aryl group or heterocyclic group, where R⁵ and R⁶ may be linked together to form a ring.

25. The guest-host mode liquid crystal cell of claim 14, wherein the content of the quinone compound is from 0.1 to 15 wt % based on the total weight of the liquid crystal compound.

26. The guest-host mode liquid crystal cell of claim 14, wherein said liquid crystal compound is a fluorine-containing liquid crystal compound.

27. The guest-host mode liquid crystal cell of claim 14, further comprising a pair of electrode substrates sandwiching said liquid crystal layer.

28. A quinone compound represented by formula (1) or (2) below:

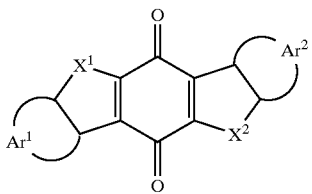

formula (1)

(wherein $X^1$ and $X^2$ independently represents an oxygen atom, sulfur atom or N—$R^1$; $R^1$ represents a hydrogen atom, alkyl group, aryl group or heterocyclic group; $Ar^1$ and $Ar^2$ independently represents an atomic group necessary for forming an aromatic ring or aromatic rings, where at least one of such aromatic rings formed by $Ar^1$ and $Ar^2$ has a substituent selected from the group consisting of alkylthio group, arylthio group, heteroarylthio group and —N($R^2$)($R^3$) group; and $R^2$ and $R^3$ independently represents a hydrogen atom, alkyl group, aryl group or heterocyclic group, where $R^2$ and $R^3$ may be linked together); and

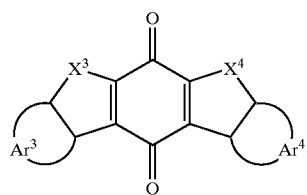

formula (2)

(wherein $X^3$ and $X^4$ independently represents an oxygen atom, sulfur atom or N—$R^4$; $R^4$ represents a hydrogen atom, alkyl group, aryl group or heterocyclic group; $Ar^3$ and $Ar^4$ independently represents an atomic group necessary for forming an aromatic ring or aromatic rings, where at least one of such aromatic rings formed by $Ar^3$ and $Ar^4$ has a substituent selected from the group consisting of alkylthio group, arylthio group, heteroarylthio group and —N($R^5$)($R^6$) group; and $R^5$ and $R^6$ independently represents a hydrogen atom, alkyl group, aryl group or heterocyclic group, where $R^5$ and $R^6$ may be linked together).

29. The quinone compound of claim 28, which is represented by said formula (1).

30. The quinone compound of claim 28, which is represented by said formula (2).

31. The quinone compound of claim 29, wherein $X^1$ and $X^2$ in the formula (1) independently represents an oxygen atom or sulfur atom.

32. The quinone compound of claim 30, wherein $X^3$ and $X^4$ in the formula (2) independently represents an oxygen atom or sulfur atom.

33. The quinone compound of claim 29, wherein both of $X^1$ and $X^2$ in the formula (1) are oxygen atoms.

34. The quinone compound of claim 30, wherein both of $X^3$ and $X^4$ in the formula (2) are oxygen atoms.

35. The quinone compound of claim 29, wherein $Ar^1$ and $Ar^2$ respectively represents an atomic group necessary for forming a substituted benzene, naphthalene or pyridine.

36. The quinone compound of claim 30, wherein $Ar^3$ and $Ar^4$ respectively represents an atomic group necessary for forming a substituted benzene, naphthalene or pyridine.

37. The quinone compound of claim 35, wherein both of $Ar^1$ and $Ar^2$ are benzene.

38. The quinone compound of claim 36, wherein both of $Ar^1$ and $Ar^2$ are benzene.

39. The quinone compound of claim 29, wherein both of $Ar^1$ and $Ar^2$ are substituted by at least one arylthio group and —N($R^2$)($R^3$) group.

40. The quinone compound of claim 30, wherein both of $Ar^3$ and $Ar^4$ are substituted by at least one arylthio group and —N($R^5$)($R^6$) group.

* * * * *